United States Patent
Kim et al.

(10) Patent No.: US 9,974,881 B2
(45) Date of Patent: May 22, 2018

(54) AIR PURIFYING APPARATUS USING ULTRA VIOLET LIGHT EMITTING DIODE

(71) Applicant: Seoul Viosys Co., Ltd., Ansan-si (KR)

(72) Inventors: Jong Rack Kim, Ansan-si (KR); Young Hwan Son, Ansan-si (KR); Seong Min Lee, Ansan-si (KR); Jae Seon Yi, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 184 days.

(21) Appl. No.: 14/761,185

(22) PCT Filed: Jan. 24, 2014

(86) PCT No.: PCT/KR2014/000725
§ 371 (c)(1),
(2) Date: Jul. 15, 2015

(87) PCT Pub. No.: WO2014/116066
PCT Pub. Date: Jul. 31, 2014

(65) Prior Publication Data
US 2015/0359922 A1    Dec. 17, 2015

(30) Foreign Application Priority Data
Jan. 25, 2013  (KR) .................. 10-2013-0008807

(51) Int. Cl.
*A61L 9/00* (2006.01)
*A61L 9/20* (2006.01)
*A61L 2/00* (2006.01)

(52) U.S. Cl.
CPC ............ *A61L 9/205* (2013.01); *A61L 2/00* (2013.01); *A61L 9/00* (2013.01); *A61L 9/20* (2013.01)

(58) Field of Classification Search
CPC ... A61L 9/00; A61L 9/20; A61L 9/205; A61L 2/00
See application file for complete search history.

(56) References Cited

U.S. PATENT DOCUMENTS 5,813,752 A * 9/1998 Singer ............... H01L 33/46
257/13
5,919,422 A * 7/1999 Yamanaka .......... A61L 2/232
422/121

(Continued)

FOREIGN PATENT DOCUMENTS

JP         3154670 U     10/2009
KR   1020070087819 A    8/2007

OTHER PUBLICATIONS

Chen, J. et al., "Photocatalytic degradation of organic wastes by electrochemically assisted Ti02 photocatalytic system", Journal of Environmental Management, Jan. 2004, vol. 70, Issue 1, pp. 43-47.

(Continued)

Primary Examiner — Sean E Conley
(74) Attorney, Agent, or Firm — Perkins Coie LLP

(57) ABSTRACT

The present invention relates to an air cleaning apparatus comprising a UVLED, which can efficiently clean air flowing in tubes by an effective combination of the UVLED and a photocatalyst and can effectively clean air flowing in a duct by enhancing the cleaning function or increasing the number of cleaning steps when the concentration of harmful substances increases. The air cleaning apparatus includes: a case comprising an inlet configured to introduce air, an outlet configured to discharge air, and a duct disposed between the air inlet and the air outlet; a photocatalyst unit disposed in the duct; and a UVLED module disposed in the duct and including a plurality of first UVLEDs arranged to irradiate UV light from the side of the inlet to the side of the outlet.

22 Claims, 7 Drawing Sheets

(56) References Cited

U.S. PATENT DOCUMENTS

| | | | | |
|---|---|---|---|---|
| 6,372,186 B1* | 4/2002 | Fencl | .................. | A61L 9/20 |
| | | | | 250/435 |
| 6,797,127 B1* | 9/2004 | Murata | .................. | A61L 9/015 |
| | | | | 204/158.2 |
| 2009/0252654 A1 | 10/2009 | Hsu et al. | | |
| 2009/0314711 A1* | 12/2009 | Barry | .................. | A01K 63/04 |
| | | | | 210/629 |
| 2011/0033346 A1 | 2/2011 | Bohlen et al. | | |
| 2012/0076700 A1* | 3/2012 | Liptak | .................. | A61L 9/205 |
| | | | | 422/186.3 |
| 2013/0034470 A1* | 2/2013 | Wang | .................. | B01D 53/8668 |
| | | | | 422/121 |

OTHER PUBLICATIONS

Han, Inho, Authorized Officer, Korean Intellectual Property Office, International Search Report, International Application No. PCT/KR2014/000725, dated Jun. 3, 2014, 2 pages.

\* cited by examiner

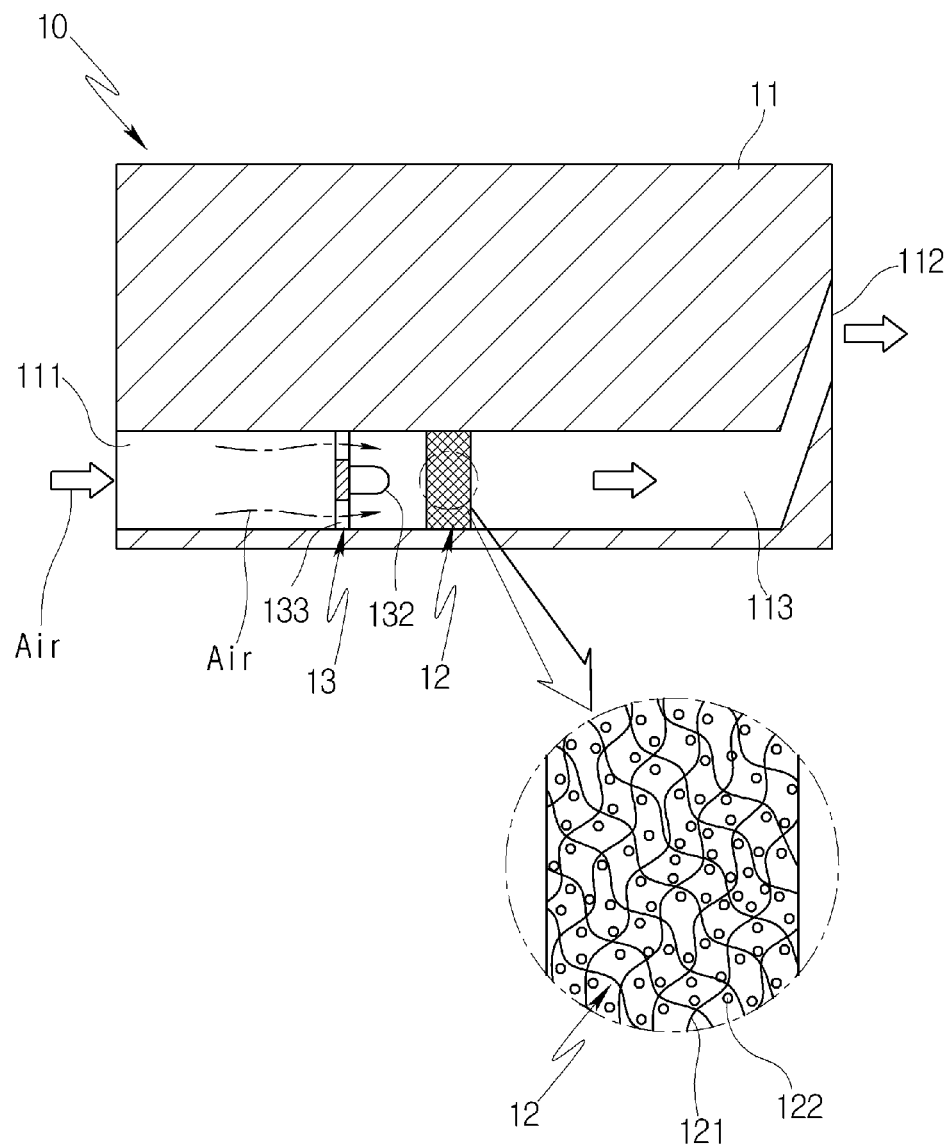

[Fig. 2]
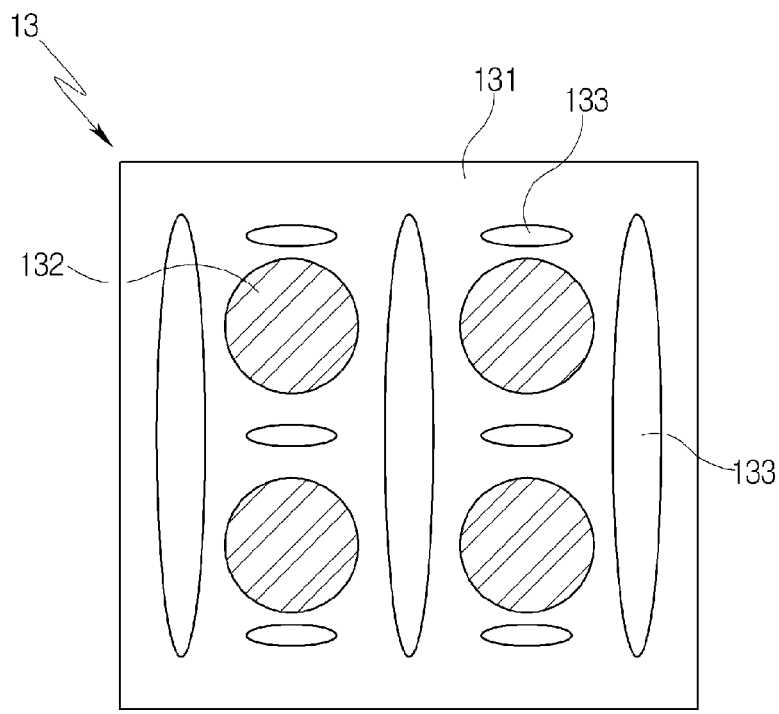
[Fig. 3]
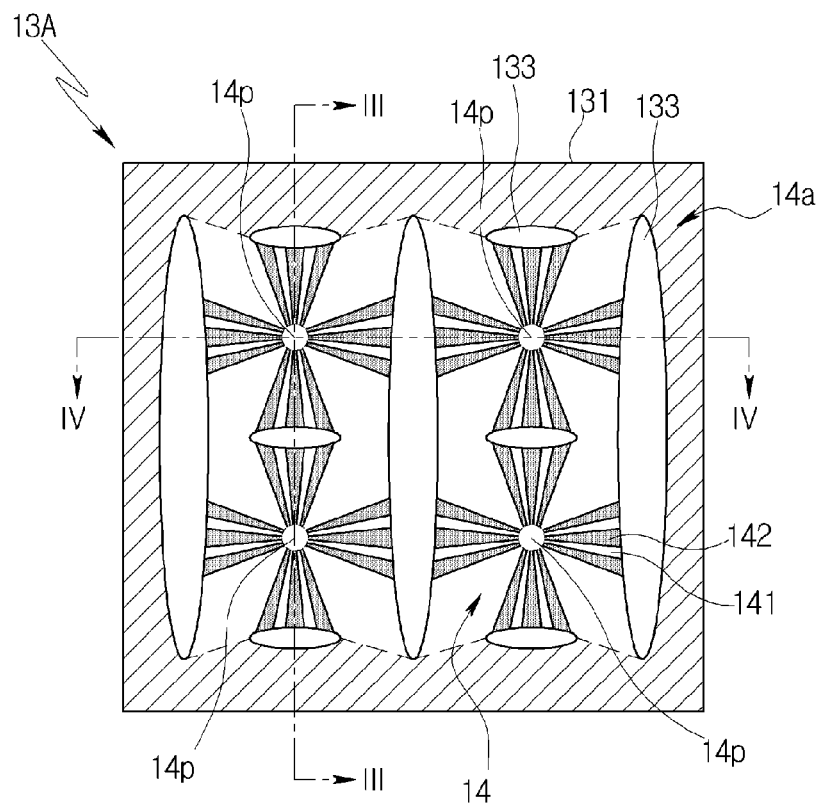

[Fig. 4]
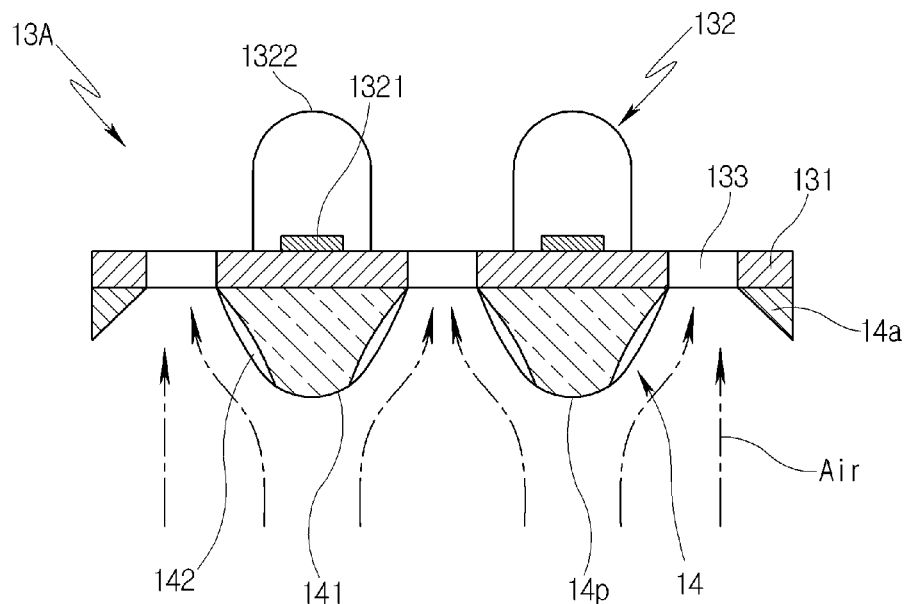
[Fig. 5]
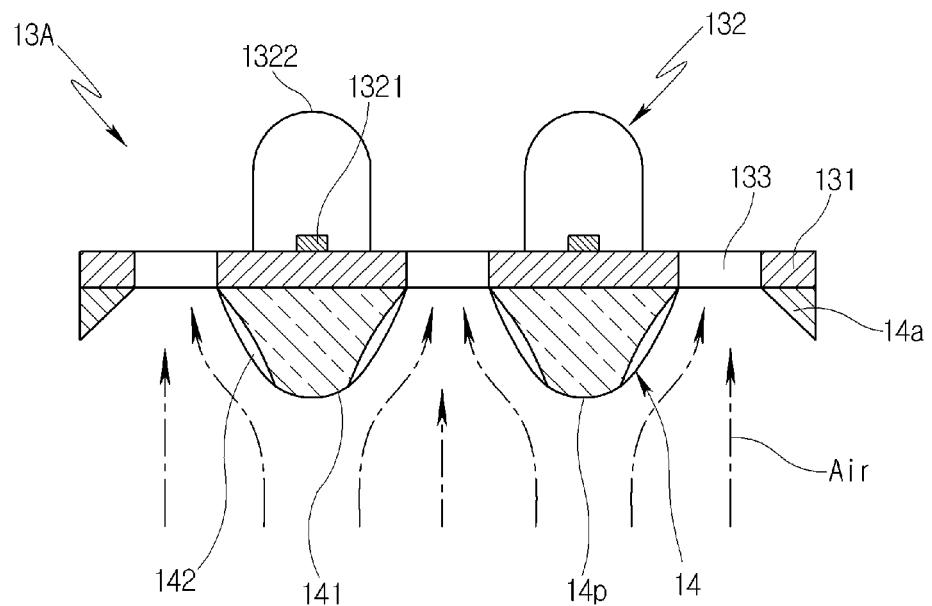

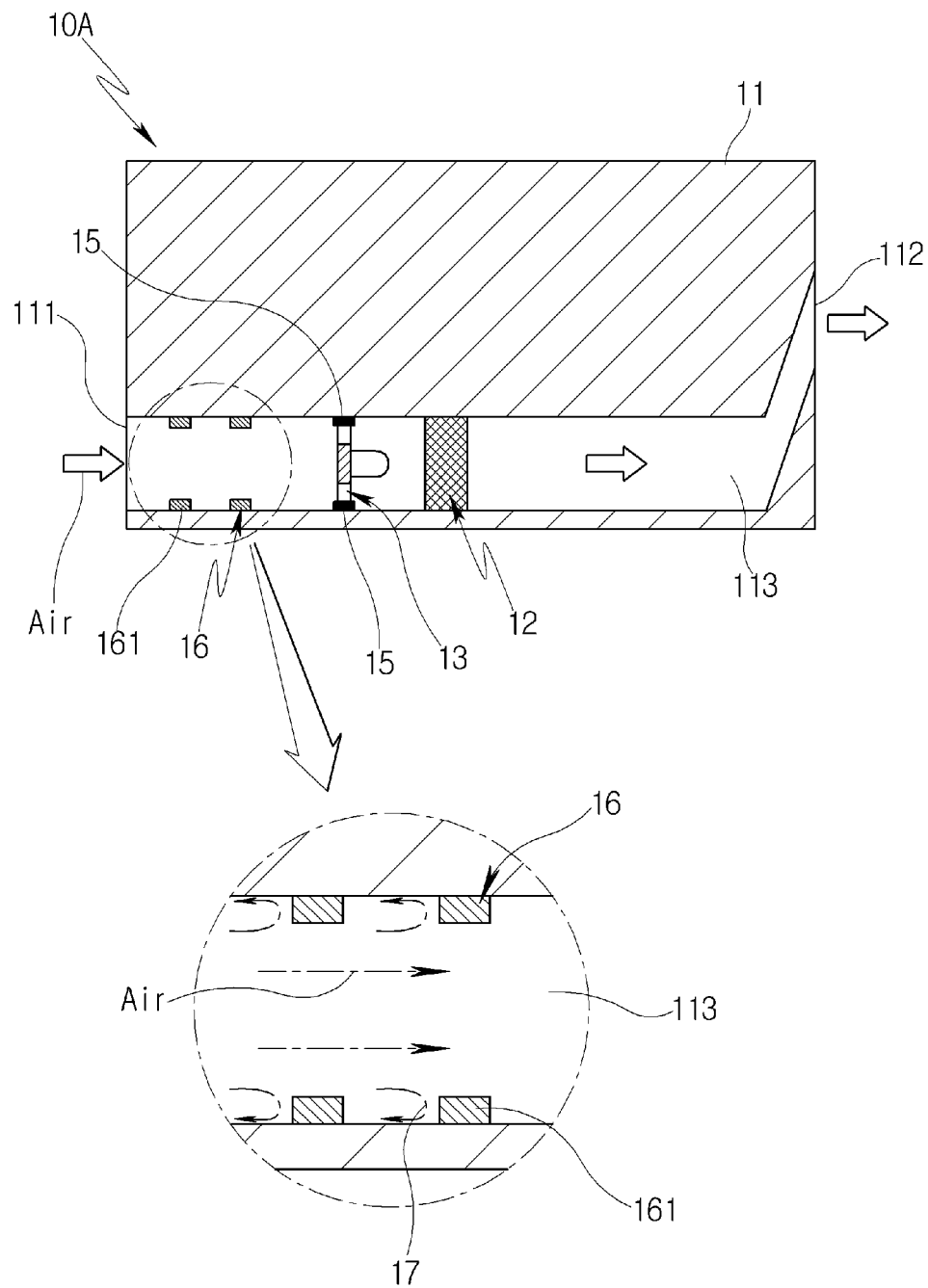

[Fig. 7]
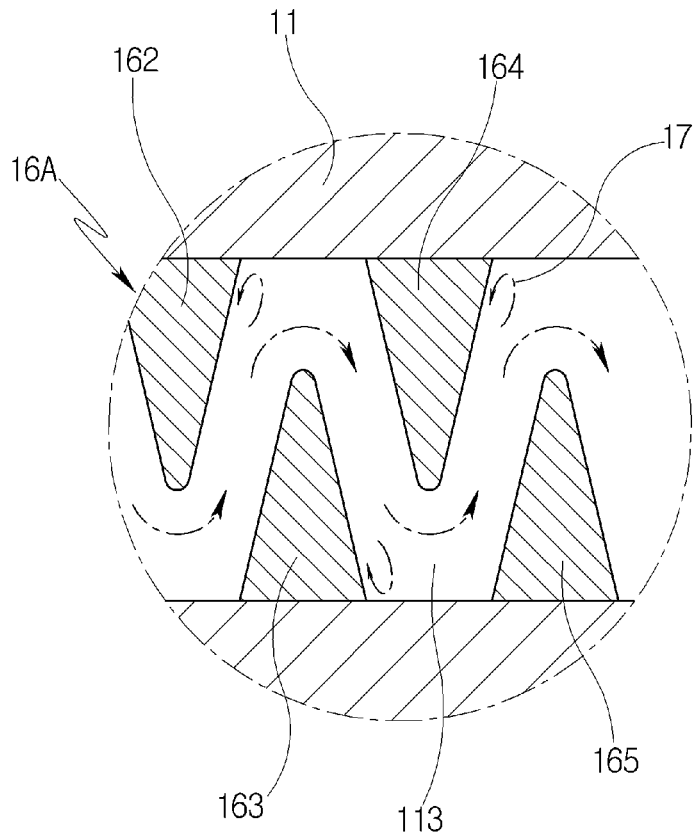
[Fig. 8]
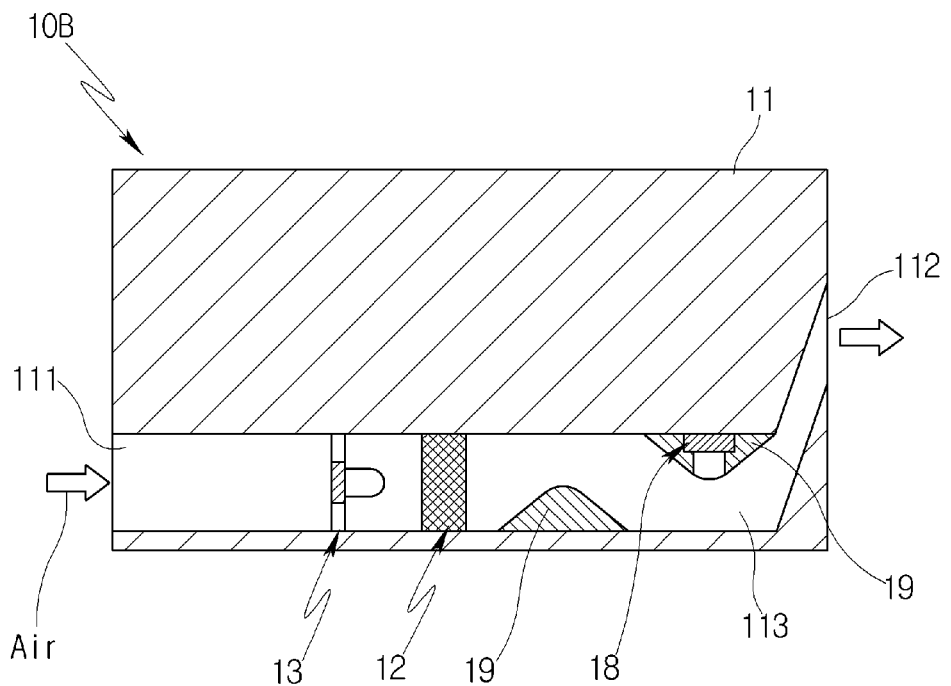

[Fig. 9]
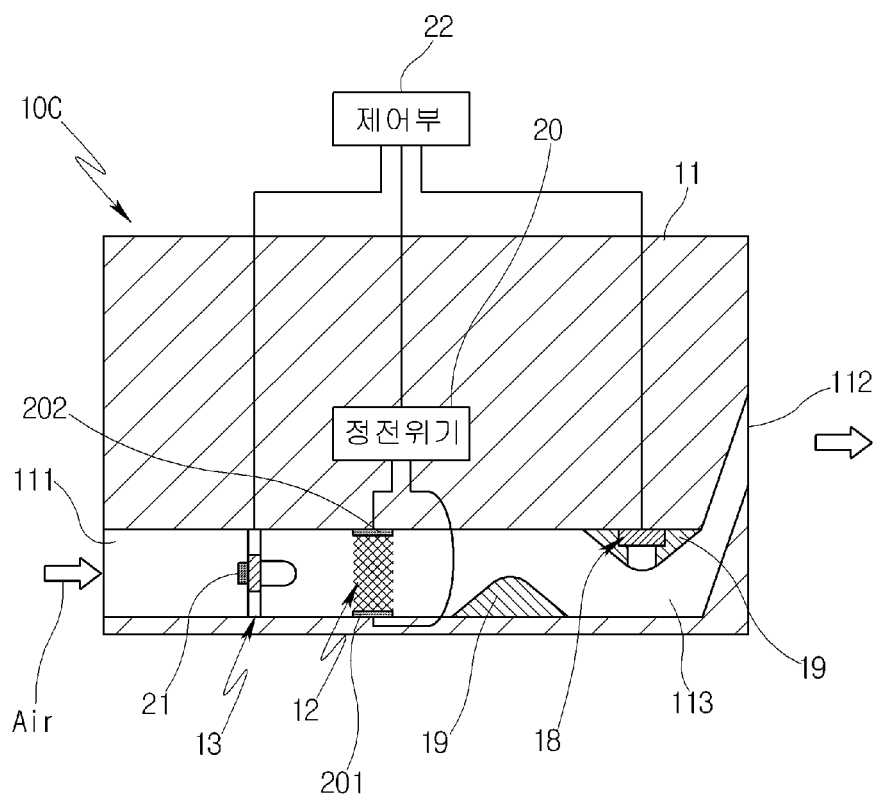
[Fig. 10]
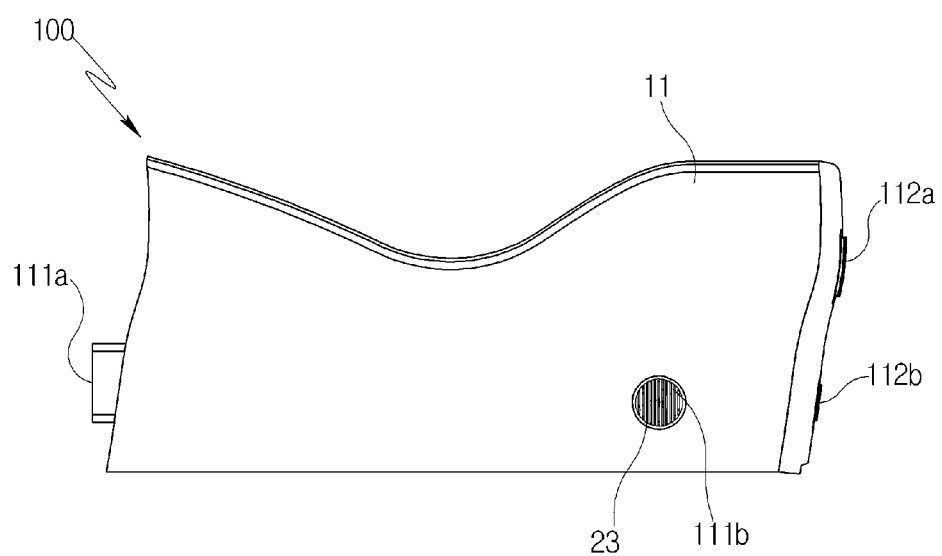

[Fig. 11]
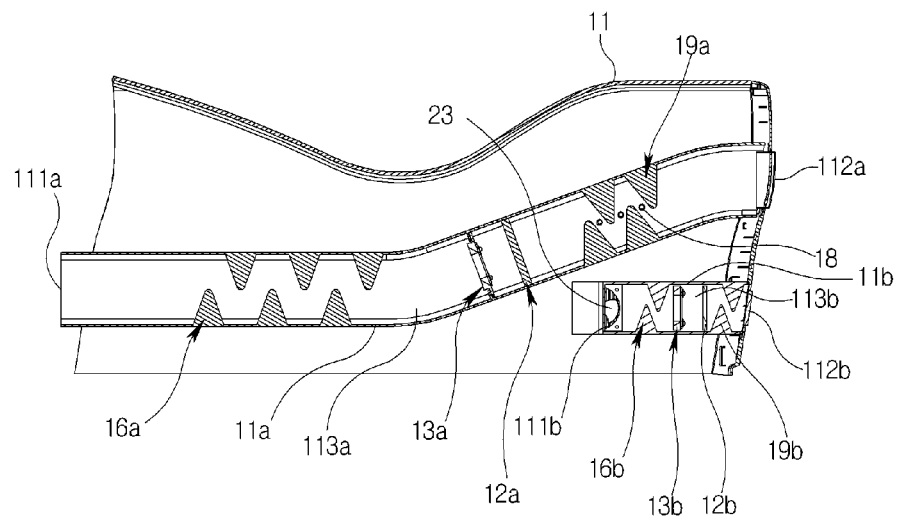
[Fig. 12]
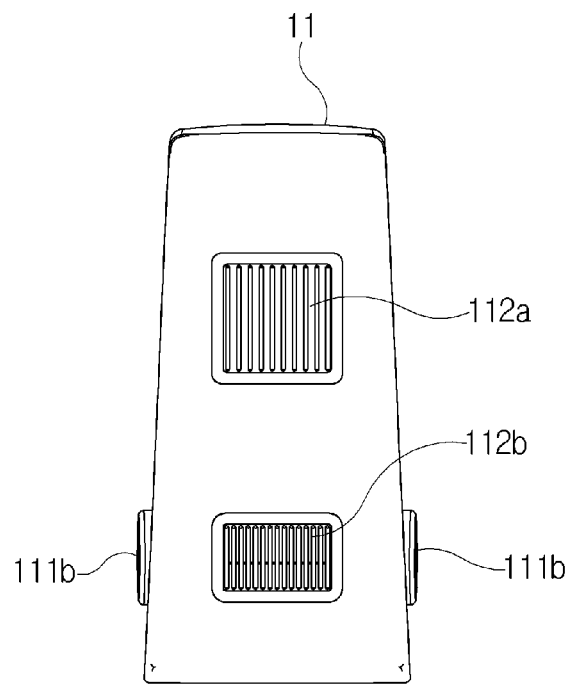

AIR PURIFYING APPARATUS USING ULTRA VIOLET LIGHT EMITTING DIODE

TECHNICAL FIELD

Exemplary embodiments of the present invention relates to an air cleaning apparatus comprising an ultraviolet light-emitting diode (UVLED), and more particularly to an air cleaning apparatus comprising a UVLED, which can efficiently clean air flowing in a duct by an effective combination of the UVLED and a photocatalyst and can effectively clean air flowing in the duct by enhancing the cleaning function or increasing the number of cleaning steps when the concentration of harmful substances increases.

BACKGROUND ART

In general, clean air, suitable temperature and suitable humidity are important factors that determine the quality of indoor environments. Due to recent urbanization and industrialization, air present in the indoor spaces of urban and industrial facilities or the closed spaces of cars may contain various harmful substances. As used herein, the term "harmful substances" refers to infectious microorganisms that spread through air, organic pollutants, atmospheric pollutants, harmful odor gases, and the like.

Such harmful substances may weaken human immunity, and in severe cases, cause various diseases, including chronic bronchitis, lung function damage, etc., and directly threaten life. Under such circumstances, in order to improve the quality of air in indoor spaces or closed spaces, various air cleaning methods have been introduced.

An example of conventional air cleaning methods includes a method of performing air cleaning by adsorbing some dusts and harmful substances contained in air by the use of a nonwoven fabric or activate carbon filter mounted in an air vent or ventilation opening located in a duct. However, this conventional technology is a method of removing harmful substances by adsorption and has shortcomings in that, because harmful substances are not decomposed, the filter is required to be periodically replaced due to adsorption, thus reducing the lifespan of the apparatus used.

Another example of conventional air cleaning methods includes an air cleaning method that uses an ionizer or the like. This air cleaning method is a method of cleaning air in, for example, cars or air conditioners, and comprises filtering harmful substances in externally introduced air that is passing through an evaporator core and a filter coated with an antimicrobial substance. However, the air cleaning method that uses the ionizer has a problem in that ozone harmful to the human body is generated.

Still another example of conventional air cleaning methods includes a method that comprises removing particles such as dust from air using a HEPA filter, and then treating air with ozone or a titanium dioxide in order to generate anions or deodorize air. In this method, there are problems in that when a high voltage is applied across an electrode in order to activate the deodorization and sterilization functions of the bulk-type titanium dioxide catalyst having a lattice structure, a high electric field is applied to a portion of the electrode to cause electric discharge, resulting in a decrease in the efficiency of the catalyst, or the use of the high voltage involves the risk of fire, limits the thickness of the catalyst and reduces the strength of the catalyst.

In order to solve the above-described problems, an air cleaning method that uses a UV lamp can be considered. However, the air cleaning method that uses a UV lamp has a limitation in that it can be applied only to a place that guarantees the durability of the UV lamp and can receive the size of the UV lamp. For example, if the air cleaning method that uses the UV lamp is applied to a car, the UV lamp can be easily broken by the vibration or impact of the car. For this reason, it is difficult to actually apply this method to cars.

In addition, an air cleaning method that uses a UV lamp and a photocatalyst has shortcomings in that the size of the UV lamp makes it difficult to miniaturize the air cleaning apparatus and in that a relatively large amount of power is consumed to activate the photocatalyst, because the UV lamp includes, in addition to a wavelength that is used for activation of the photocatalyst, a number of wavelengths that are not used for activation of the photocatalyst.

DISCLOSURE OF INVENTION

Technical Problem

An embodiment of the present invention is directed to an air cleaning apparatus comprising an ultraviolet light-emitting diode (UVLED), which efficiently cleans air flowing in a duct by an effective combination of the UVLED and a photocatalyst and a structure having increased air retention time.

Another embodiment of the present invention is directed to an air cleaning apparatus comprising a UVLED, which effectively cleans air flowing in a duct by enhancing the cleaning function or increasing the number of cleaning steps when the concentration of harmful substances is higher than a standard.

Another embodiment of the present invention is directed to an inexpensive and highly efficient air cleaning apparatus comprising a UVLED, which can be advantageously applied to car armrests and the like.

Solution to Problem

In accordance with an embodiment of the present invention, an air cleaning apparatus comprising a ultraviolet light-emitting diode (UVLED) includes: a case including an inlet configured to introduce air, an outlet configured to discharge air, and a duct disposed between the air inlet and the air outlet; a photocatalyst unit disposed in the duct; and a ultraviolet light-emitting diode (UVLED) module disposed in the duct and including a plurality of first ultraviolet light-emitting diodes (UVLEDs) arranged to irradiate UV light from the side of the inlet to the side of the outlet.

The UVLED module may further include: a substrate configured to support the plurality of first UVLEDs and including a plurality of openings provided between the plurality of first UVLEDs; and an air guide portion protruding from the substrate toward the inlet and having a conical shape, a pyramid shape, a hemispherical shape, or a combination thereof. Herein, the UVLED module may be configured such that air introduced into the duct is guided by the air guide portion, and then flows through the openings of the substrate.

The substrate may have a heat sink configured to dissipate heat from the plurality of first UVLEDs, and the heat sink may be formed integrally with the air guide portion.

The air cleaning apparatus may further include a vortex forming portion provided in the duct and configured to form vortices in the flow of air. Herein, the vortex forming portion may have a protrusion formed on the inner wall of the duct.

In addition, the vortex forming portion may have at least one pair of flow path forming portions either that are arranged to cross each other on the inner wall of the duct so as to increase the flow path of air or that protrude from the inner wall of the duct in different directions.

The photocatalyst unit may have a porous structure and a photocatalyst coated on the porous structure. Herein, the porous structure may include metal foam. The photocatalyst may include at least one material selected from among titanium dioxide (TiO2), zinc oxide (ZnO), cadmium sulfide (CdS), zirconium oxide (ZrO2), tin oxide (SnO2), vanadium oxide (V2O2), tungsten trioxide (WO3) and strontium titanate (SrTiO3).

The air cleaning apparatus may further include an elastic member interposed between the inner wall of the duct and the UVLED module.

The air cleaning apparatus may further include a second UVLED disposed following a photocatalyst region formed by the photocatalyst, the second UVLED being configured to directly sterilize air flowing in the duct by UV light.

The first UVLEDs may include UVLEDs configured to irradiate UV light having a wavelength of 400 nm or shorter as expressed by the draft ISO standard on determining solar irradiances (ISO-DIS-21348), and the second UVLED may include a UVLED configured to irradiate UV light having a wavelength between 255 nm and 300 nm.

The air cleaning apparatus may further include a flow path restricting portion that protrudes from the inner wall of the duct so as to restrict the flow path of air within the range of irradiation of UV light from the second UVLED.

The second UVLED may be provided integrally with the flow path restricting portion.

The air cleaning apparatus may further include a potentiostat configured to generate a potential difference in the photocatalyst of the photocatalyst unit. Herein, the potentiostat may have a reference electrode connected to one end of the porous structure that supports the photocatalyst, and a working electrode connected to the other end of the porous structure, and may be configured to apply a voltage to the reference electrode and the working electrode so that the photocatalyst has a predetermined potential difference.

The case may correspond to a case for at least one of an air inlet and outlet for a car armrest, an air conditioner or a heater.

The case may be a case for an armrest in a car and may include a first air cleaning unit and a second air cleaning unit, in which the first air cleaning unit may include: a first inlet and a second inlet, which correspond to the inlet; a first outlet and a second outlet, which correspond to the outlet; and a first duct corresponding to the duct and provided between the first inlet and the first outlet, and a second duct corresponding to the duct and provided between the second inlet and the second outlet. Herein, the first inlet may be connected to an air conditioner in the car, the first outlet may be disposed on a first outer surface of the case so as to be exposed to the inside of the car, the second inlet may be disposed on a second outer surface of the case so as to be exposed to the inside of the car, and the second outlet may be disposed on a third outer surface of the case so as to be exposed to the inside of the car.

The air cleaning apparatus may further include an air circulating fan disposed in the second inlet and configured to introduce air in the car into the second duct.

Advantageous Effects of Invention

The air cleaning apparatus comprising an ultraviolet light-emitting diode (UVLED) according to the present invention has the effect of efficiently cleaning air flowing in a duct by a combination of the UVLED and a photocatalyst and a structure having increased air retention time.

The air cleaning apparatus comprising a UVLED according to an embodiment of the present invention has the effect of effectively cleaning air in a duct by enhancing the cleaning function or increasing the number of cleaning steps when the concentration of harmful substances is higher than a standard.

The air cleaning apparatus comprising a UVLED according to another embodiment of the present invention can be advantageously used in car armrests or the air inlet opening or ventilation opening of air conditioners or heaters.

BRIEF DESCRIPTION OF DRAWINGS

FIG. 1 is a schematic sectional view of an air cleaning apparatus according to the present invention.

FIG. 2 is a top view of an ultraviolet light-emitting diode (UVLED) module that can be used in the air cleaning apparatus shown in FIG. 1.

FIG. 3 is a bottom view of a UVLED module for an air cleaning apparatus according to an embodiment of the present invention.

FIGS. 4 and 5 are enlarged sectional views of the UVLED module shown in FIG. 3.

FIG. 6 is a sectional view of an air cleaning apparatus according to another embodiment of the present invention.

FIG. 7 is a partial sectional view of an example of a vortex forming portion that may be used in the air cleaning apparatus shown in FIG. 6.

FIG. 8 is a sectional view of an air cleaning apparatus according to still another embodiment of the present invention.

FIG. 9 is a sectional view of an air cleaning apparatus according to still another embodiment of the present invention.

FIG. 10 is a sectional view of an air cleaning apparatus according to still another embodiment of the present invention.

FIG. 11 is a cross-sectional view of the air cleaning apparatus shown in FIG. 10.

FIG. 12 is a right side view of the air cleaning apparatus shown in FIG. 10.

MODE FOR THE INVENTION

The terms or words used in the specification and claims should not be limited to be construed as usual or dictionary definition but should be rather construed to be consistent with the technical spirits of the present invention based on the principle that the inventors may properly define the terms used in the specification to describe their invention in the best manner. Accordingly, it should be understood that the embodiments described in the specification and configurations disclosed in the drawings are merely examples and do not represent all of the technical spirits of the present invention and various modifications and variations to the present invention and equivalents thereof may be made at the time of filing of this application.

The terms used in the specification are intended to describe specific embodiments and shall not be used in a limiting sense. As used herein, the singular forms may be intended to include the plural forms, unless the context clearly dictates otherwise.

EMBODIMENTS

FIG. 1 is a schematic sectional view of an air cleaning apparatus according to the present invention.

Referring to FIG. 1, an air cleaning apparatus 10 according to the present invention comprises a case 11, a photocatalyst unit 12 and a UVLED module 13.

The case 11 comprises an air inlet 111, an air outlet 112 and a duct 113. The air inlet 111 is located at one end of the duct 113 and corresponds to an opening through which air is introduced. The air outlet 112 is located at the other end of the duct 113 and corresponds to an opening through which air is discharged. The duct 113 may correspond to either a conduit that guides air, introduced through the air inlet 111, so as to be discharged through the air outlet 112, or an air flow channel formed by the conduit. The cross section of the duct 113 may have a circular shape, a triangular shape, a rectangular or polygonal shape, or a combination thereof.

As used herein, the term "air" refers to an air that flows into the indoor spaces or closed spaces of general houses, offices, factories, cars, aircrafts, ships or the like or circulates in the spaces. This air may generally contain various harmful substances, including dust, infectious microorganisms (ticks, bacteria), organic pollutants, atmospheric pollutants (sulfur oxides, dioxin), harmful odor gases (formaldehyde, acetaldehyde, xylene, toluene, styrene), etc.

The photocatalyst unit 12 serves to oxidize harmful substances in air, which passes through the duct 113, by a photocatalyst. For the effective action of the photocatalyst, the photocatalyst unit 12 may be configured to fill or plug a portion of the middle of the duct 113. However, the photocatalyst unit 12 should be configured so as not to substantially increase the internal pressure of the duct 113. Thus, the photocatalyst unit 12 in this embodiment comprises a porous structure 121 and a photocatalyst 122.

The porous structure 121 is a carrier for supporting the photocatalyst 122. The carrier may also be referred to as a support. This photocatalyst unit 12 may correspond to one in which a catalyst composed of, for example, titanium dioxide particles supported on the porous structure is disposed in a specific region of the duct 113.

In this embodiment, the porous structure 121 has a structure for increasing the surface area and functions to increase the contact area between the photocatalyst 122 and reactants (harmful substances, etc.) to thereby increase the activity of the catalyst. Moreover, the porous structure 121 is configured to be filled in a specific region of the meddle of the duct 113. In addition, the porous structure 121 may be formed of metal foam so that the internal pressure of the duct 113 does not substantially increase.

The metal foam is a completely open porous metal structure in which all pores are connected to each other, and it has various pore sizes, low specific gravity and a high ease of use. The metal foam may be pure foam or alloy foam. Herein, the pure foam is a material prepared to have the structural properties of three dimensional open pores while maintaining the properties of base metals (Ni, Fe, Cu, etc.), and it has high reactivity due to its large specific area. In addition, the alloy foam refers to a new material prepared by applying advanced alloy technology to the fundamental properties of nickel (Ni), iron (Fe) or copper (Cu) foam.

The photocatalyst 122 functions to remove harmful substances (hydrocarbon-based organic compounds, etc.) from air by oxidation reaction with UV light. The photocatalyst 122 may be made of at least one material selected from among titanium dioxide ($TiO_2$), zinc oxide (ZnO), cadmium sulfide (CdS), zirconium oxide ($ZrO_2$), tin oxide ($SnO_2$), vanadium oxide ($V_2O_2$), tungsten trioxide ($WO_3$) and strontium titanium oxide ($SrTiO_3$). Particularly, the photocatalyst 122 is preferably $TiO_2$ (anatase, rutile) that is optically activated, does not substantially corrode, is biologically or chemically stable and is inexpensive.

For example, in an air cleaning method that uses a titanium dioxide photocatalyst having strong sterilization and oxidation properties, an oxidation/reduction reaction and a hydrophilic reaction can occur when irradiating nanometer-sized titanium dioxide crystals with UV light having a wavelength of 400 nm or shorter, and the photocatalyst surface can exhibit an effect like incineration at an absolute temperature of 30,000 K, thereby oxidizing and decomposing organic volatile compounds (VOCs) such as acetaldehyde, xylene, toluene and styrene, toxic substances such as radon gas and formaldehyde, which are generated in buildings, offensive odor gases such as hydrogen sulfide and ammonia, and atmospheric pollutants such as sulfur oxides (SOx), and oxidizing and decomposing organic chlorine compounds such as tricholorethylene, phenol compounds, polyvinyl chloride (PVC), environmental hormones (bisphenol, nonylphenol, estradiol), dioxin, acetaldehyde, xylene, toluene, styrene, hydrogen sulfide, methyl mercaptan, methyl sulfide, trimethylamine, isovalerate and ammonia, and decomposing microorganisms such as bacteria or viruses and oxidizing the decomposition products into carbon dioxide and water, and removing the toxic substances. Thus, this method has a strong air cleaning effect.

In addition, in the air cleaning method that uses the strong sterilization and oxidation properties of titanium dioxide, photocatalytic action occurs on the surface of the photocatalyst coated on a specific base, and thus the contact area between the photocatalyst and air can increase to increase the air cleaning ability of the titanium dioxide. In addition, light energy corresponding to the band gap energy of titanium dioxide can be suitably irradiated to air, thereby increasing the air cleaning ability of the titanium dioxide.

The UVLED module 13 has at least one UVLED 132 and is disposed so as to irradiate UV light from the side of the air inlet, located at one end of the duct, to the side of the air outlet located at the other end of the duct. Particularly, the UVLED module 13 is preferably configured to effectively activate the photocatalyst 122 of the photocatalyst unit 12 disposed in the middle of the duct 113. Thus, the UVLED module 13 in this embodiment is disposed to be opposite the photocatalyst unit 12 in the duct 113 such that UV light with suitable intensity can reach the photocatalyst 122 and can be irradiated to the entire region of the photocatalyst 122. Although it is shown in FIG. 1 for convenience of illustration that one UVLED 132 is disposed in the middle of the duct 113, a plurality of UVLEDs may also be used depending on the cross-sectional area of the duct 113.

Furthermore, the UVLED module 13 may have a size corresponding to the cross-sectional area of the duct 113 in order to effectively activate the photocatalyst 122 and may be disposed to be opposite the photocatalyst unit 12. In this case, the UVLED module 13 has a plurality of openings 133 for air flow so as not to substantially increase the internal pressure of the duct 113. Although it is shown in FIG. 1 for convenience of illustration that one UVLED 132 is disposed in the middle of the duct 113 and that a plurality of openings 133 are disposed between the UVLED 132 and the inner wall of the duct 113, the scope of the present invention is not limited to this configuration. In some embodiments, at least one opening may be located in the middle of the duct 113, and a plurality of UVLEDs may be disposed between the opening and the inner wall of the duct 113.

In addition, the UVLED module 13 has a power source unit or driving unit configured to supply power to the UVLED 132 or control the power supply. The power source unit or the driving unit may be suitably placed in the inside or outside of the case 11 depending on applications (car armrests, air conditions, heaters, etc.) in which the case 11 is disposed. This power source unit and driving unit are already well known in the art, and thus the detailed description thereof is omitted.

In accordance with this embodiment, there can be provided an inexpensive and highly efficient air cleaning apparatus capable of effectively removing (i.e., sterilizing, antibacterial, antifouling and deodorizing) harmful substances from air passing through a duct by means of the photocatalyst and UVLED disposed in the duct in applications (car armrests, air conditions, heaters, etc.) having the duct.

FIG. 2 is a top view of an ultraviolet light-emitting diode (UVLED) module which may be used in the air cleaning apparatus shown in FIG. 1.

Referring to FIG. 2, a UVLED module 13 for an air cleaning apparatus according to this embodiment comprises a substrate 131, a plurality of UVLEDs 132 and a plurality of openings 133.

The substrate 131 is an element on which a plurality of UVLEDs 132 and a driving unit (not shown) configured to drive the plurality of UVLEDs 132 are mounted. The substrate 131 may have a material or structure configured to dissipate heat from the plurality of UVLEDs 132. In this embodiment, the substrate 131 has a size and shape similar to those of the cross section of the duct and is disposed in the middle of the duct such that the main surface of the substrate 131 is arranged in a direction approximately perpendicular to air flow in the duct.

Each of the UVLEDs 132 is configured to emit UV light having a wavelength of 400 nm or shorter when a specific voltage is applied to both terminals of the UVLED element. The UVLEDs 132 serves to activate photocatalyst portions arranged at a specific distance in a direction in which UV light is irradiated.

In this embodiment, the plurality of UVLEDs 132 are mounted on one surface of the substrate 131. Specifically, the plurality of UVLEDs 132 are disposed so as to irradiate UV light from the side of the air inlet, located at one end of the duct, to the side of the air outlet located at the other end of the duct. In FIG. 2, four UVLEDs 132 are shown by four oblique line circles, respectively, for convenience of illustration.

The plurality of openings 133 are provided such that air introduced into the duct through the air inlet can flow from the other surface to the one surface of the substrate 131 through the openings. The plurality of openings 133 may be provided in the majority of the substrate 131 excluding the substrate region in which the plurality of UVLEDs 132 are disposed. The plurality of openings 133 are not limited to an oval shape and may be provided to have various shapes and the largest possible size in the range in which the durability of the substrate 131 is not problematic. It is shown in FIG. 2 for convenience of illustration that the plurality of openings 133 are located between four UVLEDs 132 and around four UVLEDs 132.

FIG. 3 is a bottom view of a UVLED module for an air cleaning apparatus according to an embodiment of the present invention.

Referring to FIG. 3, a UVLED module 13A for an air cleaning apparatus according to this embodiment comprises air guide portions 14 and 14a. The UVLED module 13A shown in FIG. 3 may be the same the UVLED module 13 shown in the bottom view of FIG. 2, except that it comprises the air guide portions 14 and 14a.

The air guide portions 14 and 14a are provided in the form of protruding hills between the openings 133 and around the outside of the openings 133 on the other surface of the substrate 131 of the UVLED module 13A. It is shown in FIG. 3 that some air guide portions (hereinafter referred to first air guide portions) 14 are located between the openings 133 and the remaining air guide portions 14a are located around the outside of the openings 133.

The first air guide portions 14 may protrude from the other surface of the substrate 131 toward the air inlet located at one end of the duct and have a conical shape, a pyramidal shape, a hemispherical shape, or a combination thereof. The first air guide portions 14 are provided for the UVLEDs 132, respectively.

In addition, each of the first air guide portion 14 has valley-like grooves 142 extending from the top 14p of the hill-like protruding structure 141 to the opening 133. The groove 142 is provided such that the size or cross-sectional area thereof increases as it goes from the top 14p to the opening 133.

In accordance with this embodiment, the UVLED module 13A can effectively dissipate heat from the UVLEDs 132 by the valley-like grooves 142 that are formed along the flow direction of air while increasing the surface area of the air guide portions 14.

FIGS. 4 and 5 are enlarged sectional views of the UVLED module shown in FIG. 3.

FIG. 4 may correspond to a cross-sectional view taken along line III-III of the UVLED module shown in FIG. 3, and FIG. 5 may correspond to a cross-sectional view taken along line IV-IV of the UVLED module shown in FIG. 3. The sectional view of the UVLED module in FIG. 4 and the sectional view of the UVLED module in FIG. 5 may be substantially the same, except for the differences in the diameter of the opening 133 and the length of an LED chip 1321.

Referring to FIGS. 4 and 5, a UVLED module 13A according to this embodiment comprises a substrate 131, a plurality of UVLEDs 132, a plurality of openings 133, and air guide portions 14 and 14a. Each of the UVLEDs 132 may comprise an LED chip 1321 configured to emit UV light, and a packaging member 1322 that functions to environmentally, mechanically, chemically and electrically protect the LED chip 1321 from external environments, increase light extraction efficiency and mediate heat dissipation.

In this embodiment, the UVLED module 13A may be substantially the same as the UVLED module 13 described above with reference to FIG. 2, except that it comprises the air guide portions 14 and 14a. Thus, the description of the substrate 131, the plurality of UVLEDs 132 and the plurality of openings 133 is omitted in order to avoid overlapping description.

The air guide portions 14 and 14a are provided on the other surface of the UVLED module 13A and functions to guide air flow such that air introduced into the duct through the air inlet can easily flow to the plurality of openings 133. For this, the air guide portions 14 and 14a have a structure protruding from the substrate 131 toward the air inlet (see 111 in FIG. 1) in a specific form. The structure of the air guide portions 14 provided to correspond to the UVLEDs 132 has a conical shape, a pyramid shape, a hemispherical shape, or a combination thereof. Such air guide portions 14 and 14a can function to facilitate air flow in the duct and prevent the UVLED module 13A from being damaged by the force of air flowing in the duct.

In addition, the first guide portions 14 may have a material and/or structure configured to dissipate heat from the UVLEDs 132. The UVLEDs 132 has the property of generating a larger amount of heat than light-emitting diodes that emit visible light, and for this reason, in this embodiment, the first air guide portions 14 are used to effectively dissipate heat from the UVLEDs 132.

Such first air guide portions 14 also serving as heat sinks are made of a highly thermally conductive material (metallic material, etc.) so as to suitably dissipate heat from the LED chip 1321 while they have a structure that dissipate heat by air. For example, the first air guide portions 14 may be provided such that they come into contact with the LED chip 1321 with the substrate 131 interposed therebetween or come into contact with the LED chip 1321 while having a structure integral with at least a portion of the substrate 131.

In addition, each of the first air guide portions 14 may have a hill-like protruding structure 141 and grooves 142 that extends radially from the top 14p of the protruding structure 141 to the openings 133. In this case, the groove 142 has a valley shape extending from the top 14p of the protruding structure 141 toward the surrounding openings 133.

In accordance with this embodiment, the first air guide portions 14 function to guide air flow such that air introduced into the duct through the air inlet of the case is easily introduced into the openings 133 of the substrate 131. Further, the first air guide portions 14 have a surface area enlarged by the protruding structure 141 and the grooves 142 and can maximize heat dissipation efficiency by air flowing along the grooves 142.

FIG. 6 is a sectional view of an air cleaning apparatus according to another embodiment of the present invention.

Referring to FIG. 6, an air cleaning apparatus 10A according to this embodiment comprises a case 11, a photocatalyst unit 12, a UVLED module 13, an elastic member 15 and a vortex forming portion 16.

The air cleaning apparatus 10A according to this embodiment is substantially the same as the air cleaning apparatus 10 described above with reference to FIG. 1, except that it comprises the elastic member 15 and the vortex forming portion 16. Thus, the description of the substrate 131, the plurality of UVLEDs 132 and the plurality of openings 133 is omitted in order to avoid overlapping description.

The elastic member 15 functions to protect the UVLED module 13 disposed in the duct 113 from external vibration or impact. In other words, the elastic member 15 functions to prevent the UVLED module 13 from being impacted or damaged by the shaking of the duct 11 or the high flow rate of air. This elastic member 15 may be attached to at least a portion of the edge of the UVLED module 13 or interposed between the UVLED module 13 and a coupling portion on the duct when disposing the UVLED module 13 in the duct 113.

The vortex forming portion 16 functions to generate vortices 17 in air that flows in the duct 113 in one direction. The vortex forming portion 16 is provided on the inner wall of the duct 113 such that air can collide against the vortex forming portion 16 in the duct 113. This vortex forming portion 16 has at least one protrusion 161 protruding from the inner wall of the duct 113. The protrusion 161 that is a member protruding from the inner wall of the duct 113 to a specific height may be formed integrally with the duct 13 during the manufacture of the duct 113 or may be attached to the inner wall of the duct 113 by a separate member.

The air cleaning apparatus 10A according to this embodiment may comprise the air guide portions 14 and 14a shown in FIGS. 3 to 5.

In accordance with this embodiment, the use of the vortex forming portion interferes with the linear flow of air in the duct to form vortices and increase the retention time of air in the duct, so that air can be distributed relatively uniformly throughout the entire region of the photocatalyst unit 12, whereby harmful substances in air can easily contact come into contact with the photocatalyst, thereby increasing the efficiency with which harmful substances in the air are removed by the photocatalyst.

FIG. 7 is a partial sectional view of an example of a vortex forming portion which can be used in the air cleaning apparatus shown in FIG. 6.

Referring to FIG. 7, a vortex forming portion 16A according to this embodiment comprises a plurality of flow path forming portions 162, 163, 164 and 165 configured to form vortices and increase the retention time of air.

The first to fourth flow path forming portions 162 protrude from the inner wall of the duct 113 in different directions. Specifically, the first to fourth flow path forming portions 162 are arranged to cross each other when viewed from the cross section, in a manner similar to that the two saw teeth cross each other. In other words, the first to fourth flow path forming portions 162 may comprise oval-shaped diaphragm structures that protrude alternately in opposite directions so as to partially block the cross section of the duct 113 depending on the shape of the cross section of the duct 113.

The vortex forming portions according to this embodiment can function to interfere with the linear flow of air in the duct to form vortices and increase the retention time of air in the duct.

FIG. 8 is a sectional view of an air cleaning apparatus according to another embodiment of the present invention.

Referring to FIG. 8, an air cleaning apparatus 10B according to this embodiment comprises a case 11, a photocatalyst unit 12, a UVLED module 13, a second UVLED 18 and a flow path restricting portion 19.

The air cleaning apparatus 10B according to this embodiment is substantially the same as the air cleaning apparatus 10 described above with reference to FIG. 1, except that it comprises the second UVLED 18 and the flow path restricting portion 19. Thus, the description of the substrate 131, the plurality of UVLEDs 132 and the plurality of openings 133 is omitted to avoid overlapping description.

The second UVLED 18 is configured to emit UV light having a wavelength between 255 nm and 300 nm when a specific voltage is applied to both terminals of the UVLED element. The second UVLED 18 functions to irradiate harmful substances in air flowing in the duct 113 so as to oxidize the harmful substances.

The second UVLED 18 may be connected to a power supply unit or driving unit configured to supply power or control driving. The power supply unit or the driving unit may be suitably placed in the inside or outside of the case 11 depending on applications (car armrests, air conditions, heaters, etc.) in which the case 11 is disposed. This power source unit and driving unit function to supply power to the UVLEDs or control driving and are already well known in the art, and thus the detailed description thereof is omitted.

The flow path restricting portion 19 is disposed in the duct 113 in order to restrict the path of air flow to the range of irradiation of UV light from the second UVLED 18. The flow path restricting portion 19 is configured to restrict the path of air flow in the duct 113 so that air passing through the photocatalyst unit 12 can pass through the vicinity of the second UVLED 18. The flow path restricting portion 19 may have a structure and shape similar to those of the flow path forming portion 16A described above with reference to FIG. 7.

If the flow path restricting portion 19 is provided, the second UVLED 18 may be provided integrally with the flow path restricting portion 19 for convenience of installation, maintenance and control. Providing the second UVLED 18 integrally with the flow path restricting portion 19 can be achieved by modifying the packaging structure of the second UVLED 18 or burying the second UVLED 18 in the flow path restricting portion 19.

According to this embodiment, the second UVLED configured to secondarily remove harmful substances from air by direct irradiation of UV light is disposed in addition to a combination of the photocatalyst unit configured to primarily remove harmful substances from air passing through the duct by photocatalytic action and the UVLED module, whereby the level of the air cleaning function of the apparatus can be adjusted according to the concentration of harmful substances in air flowing into the duct, thereby effectively removing the harmful substances.

Meanwhile, in some embodiments, the air cleaning apparatus 10B according to this embodiment may comprise the air guide portions 14 and 14a shown in FIGS. 3 to 5. Further, in some embodiments, the air cleaning apparatus 10B according to this embodiment may comprise at least one of the elastic member 15 and the vortex forming portion 16 or 16A described above with reference to FIG. 6 or 7.

FIG. 9 is a sectional view of an air cleaning apparatus according to still another embodiment of the present invention.

Referring to FIG. 9, an air cleaning apparatus 10C according to this embodiment comprises a case 11, a photocatalyst unit 12, a UVLED module 13, a second UVLED 18, a flow path restricting portion 19 and a potentiostat 20. In addition, in some embodiments, the air cleaning apparatus 10C may further comprise a harmful substance detection sensor 21 and a control unit 22.

The air cleaning apparatus 10C according to this embodiment is substantially the same as the air cleaning apparatus 10B described above with reference to FIG. 8, except that it comprises the potentiostat 20, the harmful substance detection sensor 21 and the control unit 22. Thus, the description of the case 11, the photocatalyst unit 12, the UVLED module 13, the second UVLED 18 and the flow path restricting portion 19 is omitted in order to avoid overlapping description.

The potentiostat 20 is configured to apply electrostatic potential to the photocatalyst unit 12 so as to prevent the recombination of holes and electrons in the photocatalyst, thereby maintaining the activity of the photocatalyst.

In this embodiment, the potentiostat 20 comprises a reference electrode 201 connected to one end of the photocatalyst unit 12, that is, one end of the porous support that supports the photocatalyst, and a counter electrode 202 connected to the other end of the photocatalyst unit 12, that is, the other end of the porous support that supports the photocatalyst. The potentiostat 20 is configured to apply a voltage from a battery cell or a specific power source to the reference electrode 201 and the counter electrode 202.

When the potentiostat 20 is used, the photocatalyst supported on the porous structure can be activated by UV light irradiated from the UVLED module 13, and the activity of the photocatalyst can be maintained by the potentiostat 20. Thus, the time required to drive the UVLED module 13 in order to maintain the activity of the photocatalyst can be reduced, thereby reducing the power consumption of the apparatus. In addition, if titanium dioxide that is a photocatalyst is used in a fixed form, there can be a problem in that the recombination rate of ions in the photocatalyst titanium dioxide activated by UV light increases, resulting in a decrease in efficiency. In the present invention, the occurrence of this problem can be prevented.

The harmful substance detection sensor 21 is configured to measure the concentration of a specific harmful substance in air introduced into the duct 113. The harmful substance detection sensor 21 that is used in the present invention may be a conventional sensor that can measure the concentration of at least one target harmful substance by selectively detecting and capturing the harmful substance using an organic or inorganic receptor.

For convenience of illustration and explanation, this embodiment illustrates that the harmful substance detection sensor 21 is attached to the UVLED module 13, but the scope of the present invention is not limited to this configuration. Specifically, the harmful substance detection sensor 21 may also be disposed either in the vicinity of the air inlet 111 or in a specific region of a system (car, air conditioner, heater, etc.) in which the case 11 is mounted.

The control unit 22 is configured to supply power to the UVLED module 13 or control the operation of the UVLED module 13. In addition, it is configured to control the operation of the potentiostat 20 and supply power to the second UVLED 18 or control the operation of the second UVLED 18. If the air cleaning apparatus 10C is mounted in a car armrest or the like, the control unit 22 may correspond either to at least a functional portion of an electronic control unit in the car or to at least an element of the electronic control unit, which performs a function corresponding to that of this functional portion.

When the control unit 22 is used, air flowing in the duct can be effectively cleaned by enhancing the air cleaning function or increasing the number of air cleaning steps according to operating environments (e.g., a state in which the concentration of harmful substances in the duct is higher than a standard) such as the concentration of harmful substances in air.

FIG. 10 is a front view of an air cleaning apparatus according to still another embodiment of the present invention. FIG. 11 is a cross-sectional view of the air cleaning apparatus shown in FIG. 10, and FIG. 12 is a right side view of the air cleaning apparatus shown in FIG. 10.

Referring to FIGS. 10 to 12, an air cleaning apparatus 100 according to this embodiment comprises a case 11 composed of a car armrest. In this embodiment, when the case 11 is a car armrest, the air cleaning apparatus 100 comprises: a first air cleaning unit configured to remove harmful substances from air into the car from the air conditioner of the car; and a second air cleaning unit configured to remove harmful substances from air that circulates in the car.

The first air cleaning unit comprises: a conduit 11a comprising a first inlet 111a, a first outlet 112a and a first duct 113a; a first vortex forming portion 16a; a first UVLED module 13a; a first photocatalyst unit 12a; a second UVLED 18; and a first flow path restricting portion 19a.

The second air cleaning unit comprises: a conduit 11b comprising a second inlet 111b, a second outlet 112b and a second duct 113b; a second vortex forming portion 16b; a second UVLED module 13b; a second photocatalyst unit 12b; and a second flow path restricting portion 19b.

The constituent elements of each of the first air cleaning unit and the second air cleaning unit in this embodiment are substantially the same as the corresponding elements of the above-described embodiments, except that the second UVLED 18 is not integrally formed with the first flow path restricting portion 19a and that an air circulating fan 23 is disposed in the second inlet 111b. Thus, the detailed description of the same elements is omitted in order to avoid overlapping description.

Meanwhile, in some embodiments, the air cleaning apparatus 100 may further comprise at least one of the potentiostat 20 and control unit 22 described above with reference to FIG. 9.

According to this embodiment, the air cleaning apparatus is provided in a car armrest, whereby it can efficiently remove harmful substances not only from cold or hot air introduced from the air conditioner of the car, but also from air circulating in the car.

While the present invention has been described with respect to the specific embodiments, it will be apparent to those skilled in the art that various changes, substitutions and modifications may be made without departing from the spirit and scope of the invention as defined in the following claims.

INDUSTRIAL APPLICABILITY

The present invention relates to an air cleaning apparatus comprising a UVLED, which can efficiently clean air flowing in a duct by an effective combination of the UVLED and a photocatalyst, in order to improve the quality of air in indoor spaces or closed spaces in circumstances.

The invention claimed is:

1. An air cleaning apparatus comprising:
a case comprising an inlet configured to introduce air, an outlet configured to discharge air, and a duct disposed between the inlet and the outlet;
a photocatalyst unit disposed in the duct; and
an ultraviolet light-emitting diode (UVLED) module disposed in the duct and comprising at least one first ultraviolet light-emitting diode (UVLED) arranged to irradiate UV light toward an air flowing through the duct;
a substrate arranged in the duct and configured to support the at least one first UVLED; and
an air guide portion protruding from the substrate toward the inlet and having a curved sidewall,
a groove in the air guide portion, the grove depressed inwardly from the curved sidewall;
wherein the air guide has a surface area increasing along a direction of an air flow.

2. The air cleaning apparatus of claim 1, wherein
the substrate has an opening provided around the at least one first UVLEDs; and
the air guide portion
is configured to guide air introduced into the duct to flow through the opening of the substrate.

3. The air cleaning apparatus of claim 1, wherein the substrate has a heat sink configured to dissipate heat from the first UVLED, and the heat sink is formed integrally with the air guide portion.

4. The air cleaning apparatus of claim 1, further comprising a vortex forming configured to form vortices in the flow of air.

5. The air cleaning apparatus of claim 4, wherein the vortex forming portion has a protrusion formed on the inner wall of the duct.

6. The air cleaning apparatus of claim 4, wherein the vortex forming portion has a pair of flow path forming portions that are arranged to increase the flow path of air.

7. The air cleaning apparatus of claim 1, wherein the photocatalyst unit has a porous structure and a photocatalyst coated on the porous structure.

8. The air cleaning apparatus of claim 7, wherein the porous structure comprises metal foam.

9. The air cleaning apparatus of claim 7, wherein the photocatalyst comprises titanium dioxide ($TiO_2$), zinc oxide ($ZnO$), cadmium sulfide ($CdS$), zirconium oxide ($ZrO_2$), tin oxide ($SnO_2$), vanadium oxide ($V_2O_2$), tungsten trioxide ($WO_3$) or strontium titanate ($SrTiO_3$).

10. The air cleaning apparatus of claim 1, further comprising an elastic member interposed between the inner wall of the duct and the UVLED module.

11. The air cleaning apparatus of claim 1, further comprising a second UVLED disposed between the photocatalyst unit and the outlet and configured to sterilize air flowing in the duct by UV light.

12. The air cleaning apparatus of claim 11, wherein the first UVLED is configured to irradiate UV light having a wavelength of 400 nm or shorter, and the second UVLED is configured to irradiate UV light having a wavelength between 255 nm and 300nm.

13. The air cleaning apparatus of claim 11, further comprising a flow path restricting portion that protrudes from the inner wall of the duct so as to restrict the flow path of air within the range of irradiation of UV light from the second UVLED.

14. The air cleaning apparatus of claim 13, wherein the second UVLED is provided integrally with the flow path restricting portion.

15. The air cleaning apparatus of claim 1, further comprising a potentiostat configured to generate a potential difference in the photocatalyst unit.

16. The air cleaning apparatus of claim 15, wherein the potentiostat comprises a reference electrode connected to the photocatalyst unit and a counter electrode connected to the other end of the photocatalyst unit, and configured to apply different voltages to the reference electrode and the counter electrode.

17. The air cleaning apparatus of claim 15, wherein the case is disposed in a car including armrest, an air conditioner, or a heater.

18. An air cleaning apparatus comprising:
a case having an inlet configured to introduce air, an outlet configured to discharge air, and a duct disposed between the inlet and the outlet;
a photocatalyst unit disposed in the duct; and
a first ultraviolet light-emitting diode (UVLED) arranged in the duct to face the photocatalyst unit and irradiating UV light toward the photocatalyst unit, the first UV LED located between the inlet and the photocatalyst unit;
a second UVLED disposed in the duct and irradiating UV light toward an air flowing in the duct, the second UVLED located between the photocatalyst unit and the outlet; and
a flow path restriction portion disposed around the second UVLED and located to restrict an amount of the air flowing in the duct, the flow path restriction portion protruding inwardly from an inner wall of the duct.

19. The air cleaning apparatus of claim 18, wherein the first UVLED is configured to irradiate UV light having a wavelength of 400 nm or shorter and the second UVLED is configured to irradiate UV light having a wavelength between 255 nm and 300 nm.

20. The air cleaning apparatus of claim 18, further comprising:
   a substrate arranged in the duct and configured to support the first UVLED; and
   an air guide portion protruding from the substrate toward the inlet and having a curved sidewall,
   wherein the air guide portion has a groove depressed inwardly from the curved sidewall and has a surface area increasing along a direction of an air flow.

21. The air cleaning apparatus of claim 20, wherein the substrate has a heat sink configured to dissipate heat from the first UVLED, and the heat sink is formed integrally with the air guide portion.

22. The air cleaning apparatus of claim 18, further comprising a vortex forming configured to form vortices in the duct.

\* \* \* \* \*